(12) United States Patent
Garwin

(10) Patent No.: US 8,975,038 B2
(45) Date of Patent: *Mar. 10, 2015

(54) METHOD FOR DETERMINING PRESENCE OF CARCINOMIC CELLS WITH 5, 10, 15, 20-TETRAKIS (CARBOXYPHENYL) PORPHINE

(71) Applicant: Biomoda, Inc., Albuquerque, NM (US)

(72) Inventor: Jeffrey Garwin, Chapel Hill, NC (US)

(73) Assignee: bioAffinity Technologies, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/943,476

(22) Filed: Jul. 16, 2013

(65) Prior Publication Data

US 2014/0162287 A1 Jun. 12, 2014

Related U.S. Application Data

(60) Division of application No. 13/158,595, filed on Jun. 13, 2011, now Pat. No. 8,486,656, which is a division of application No. 12/715,627, filed on Mar. 2, 2010, now Pat. No. 7,960,138, which is a continuation of application No. 12/133,855, filed on Jun. 5, 2008, now Pat. No. 7,670,799, which is a division of application No. 10/933,140, filed on Sep. 2, 2004, now Pat. No. 7,384,764, which is a division of application No. 09/989,092, filed on Nov. 19, 2001, now Pat. No. 6,838,248.

(60) Provisional application No. 60/249,505, filed on Nov. 17, 2000.

(51) Int. Cl.
*G01N 33/574* (2006.01)

(52) U.S. Cl.
USPC .................................. 435/7.23; 435/40.5

(58) Field of Classification Search
USPC .................................. 435/7.23, 40.5
See application file for complete search history.

(56) References Cited

U.S. PATENT DOCUMENTS

| | | | |
|---|---|---|---|
| 4,485,086 A | 11/1984 | Wong | |
| 4,783,529 A | 11/1988 | Lavallee et al. | |
| 4,857,300 A | 8/1989 | Maksem | |
| 4,930,516 A | 6/1990 | Alfano | |
| 5,004,811 A | 4/1991 | Bommer | |
| 5,162,231 A * | 11/1992 | Cole et al. | 436/64 |
| 5,391,547 A * | 2/1995 | Cole et al. | 514/184 |
| 6,190,877 B1 | 2/2001 | Adair | |
| 6,316,215 B1 | 11/2001 | Adair et al. | |
| 6,643,041 B1 | 11/2003 | Ikeda et al. | |
| 6,838,248 B2 * | 1/2005 | Garwin | 435/7.23 |
| 6,984,498 B2 | 1/2006 | Adair | |
| 7,110,808 B2 * | 9/2006 | Adair | 600/431 |
| 7,384,764 B2 * | 6/2008 | Garwin | 435/40.5 |
| 7,670,799 B2 * | 3/2010 | Garwin | 435/40.5 |
| 7,960,138 B2 * | 6/2011 | Garwin | 435/40.5 |
| 8,486,656 B2 * | 7/2013 | Garwin | 435/40.5 |
| 2002/0115121 A1 | 8/2002 | Garwin | |
| 2004/0202612 A1 | 10/2004 | Adair | |
| 2005/0079561 A1 * | 4/2005 | Garwin | 435/7.23 |
| 2005/0233410 A1 | 10/2005 | Gar | |
| 2006/0058683 A1 | 3/2006 | Chance | |
| 2007/0172392 A1 | 7/2007 | Sen | |
| 2009/0004690 A1 | 1/2009 | Garwin | |
| 2010/0216169 A1 | 8/2010 | Garwin | |
| 2011/0014647 A1 * | 1/2011 | Dorian et al. | 435/40.5 |
| 2012/0149057 A1 | 6/2012 | Garwin | |

FOREIGN PATENT DOCUMENTS

| | | |
|---|---|---|
| EP | 2372361 | 10/2011 |
| EP | 1364044 | 1/2012 |
| JP | 08-245480 | 9/1996 |
| JP | 4307070 | 5/2009 |
| WO | 91/19977 | 12/1991 |
| WO | 91/19978 | 12/1991 |
| WO | 92/06097 | 4/1992 |
| WO | 02/42267 | 5/2002 |
| WO | 2011/009137 | 1/2011 |

OTHER PUBLICATIONS

Kancherla, K. et al., "Early Lung Cancer Detection using Nucleua Segmentation based Features", 2013 IEEE Symposium on Computational Intelligence in Bioinformatics and Computational Biology, 2013, 91-95.

Kancherla, K. et al., "Lung Cancer Detection Using Labeled Sputum Sample: Multi Spectrum Approach", Modern Approaches in Applied Intelligence, 2011, 446-458.

Kancherla, K. et al., "Non Intrusive and Extremely Early Detection of Lung Cancer Using TCPP", 2009 Fourth International Multi-Conference on Computing in the Global Information Technology, IEEE Computer Society, 2009, 104-108.

Bartocci, C. et al., "A spectrosphotometric investigation on iron(III)protoporphyrin-IX in water/alcohol/pyridine solvent systems", Inorg. Chim. Acta. vol. 37, No. 1, 1979, L473-L476.

Berns, Michael W. et al., "In Vitro Cellular Effects of Hematoporphyrin Derivative", Cancer Research vol. 42, No. 6, 1982, 2325-2328.

Boring, Catherine C., "Cancer Statistics", CA Cancer J Clin vol. 43, No. 1, 1993, 7-26.

Bunseki, Kagaku, "Reversed-Phase Partition Chromatography for Trace Copper (II), Zinc (II), Manganese (II), and Cobaldt (II) Using Tetrakis (4-Carboxyphenyl) Porphine", The Japan Society for Analytical Chemistry vol. 35, No. 9, 1986, 829-831.

(Continued)

Primary Examiner — Ralph Gitomer
(74) Attorney, Agent, or Firm — Peacock Myers, P.C.; Janeen Vilven

(57) ABSTRACT

Presented is a method of determining the presence of carcinomic cells in a sample by contacting a sample of cells with a solution of TCPP to permit binding of the TCPP to components of the abnormal dysplastic or carcinomic cells, if any are present; detecting TCPP fluorescence in the sample, the presence of TCPP fluorescence being indicative that the sample contains dysplastic or carcinomic cells.

1 Claim, No Drawings

(56) References Cited

OTHER PUBLICATIONS

Clarke, Suzanne E. et al., "Aqueous Complexation Equilibria of Meso Tetrakis(4-carboxyphenyl)porphyrine with Violgens", J of Physical Chemistry vol. 106, No. 13, 2002, 3235-3242.

Cole, D. A. et al., "Copper-67 Labeled Porphyrin Localization in Inflamed Tissue", Copper Bioavailability and Metabolism, 1990, 259-272.

Cole, D. A. et al., "The Biological Characteristics of a Water Soluble Porphyrin in Rat Lymph Nodes", Nucl. Med. Biol. Vole. 17, No. 5, 1990, 457-464.

Cortese, Denis A. et al., "Hematoporphyrin Derivative in the Detection and Localization of Radiographically Occult Lung Cancer", Am. Rev. Respir. Dis. vol. 126, No. 1, 1992, 1087-1088.

Dellinger, M. et al., "Cellular Uptake of Hydroxyethylvinyldeuteroporphyrin and Photoinactivation of Cultivated Human Leukemia (REH6) Cells", Biological Abstracts, 82:8, 1986, Philadelphia, PA, US; Abstract No. 75075, Abstract p. AB-679 of Photochem. Photobiol., 43:6, 1986, 639-648.

Ferguson, Mark K., "Diagnosing and Staging on Non-Small Cell Lung Cancer", Hematol Oncol Clin N AM vol. 4, No. 6, 1990, 1053-1068.

Firnau, G. et al., "Cu Labeling of Hematoporphyrin Derivative for Non-Invasive In-Vivo Measurement of Tumor Uptake", Porphyrin Localization and Treatment of Tumors, 1984, 629-636.

Hambright, P. et al., "The Distribution of Various Water Soluble Radioactive Metalloporphyrins in Tumor Bearing Mice", Bioinorganic Chemistry vol. 5, 1975, 87-92.

Haroske, G. et al., "Frequency and Diagnostic Reliabilty of Subvisual Morphologic Markers for Malignancy in the Cervical Epithelium", Arch Geschwulsfforsch vol. 58, No. 3, 1988, 159-168.

Hirsch, Fred R. et al., "Prevention and Early Detection of Lung Cancer-Clinical Aspects", Lung Cancer vol. 17, 1997, 163-174.

Hutchinson, Martha L. et al., "Measurement fo Subvisual Changes in Cervical Squamous Metaplastic Cells for Detecting Abnormality", Anal. Quant. Cytol. Estol. vol. 14, No. 4, 1992, 330-334.

Igarashi, Shukuro et al., "Reversed phase-partition mode HPLC for small amounts of copper (II), zinc (II), manganese (II) and cobalt (II) with $\alpha$, $\beta$, $\gamma$, $\delta$-tetrakis (4-carboxyphenyl) porphine", Bunseki Kagaku (Analytical Chemistry) vol. 35, No. 9, 1986, 829-831.

Kato, Harubumi et al., "Early Detection of Lung Cancer by Means of Hematoporphyrin Derivative Fluorescence and Laser Photoradiation", Clinics in Chest Medicine vol. 6, No. 2, 1985, 237-253.

Mao, Li et al., "Detection of Oncogene Mutations in Sputum Precedes Diagnosis of Lung Cancer", Cancer Research vol. 54, 1994, 1634-1637.

Mao, Li et al., "Microsatellite Alterations as Clonal Markers for the Detection of Human Cancer", Proc. Natl. Acad. Sci. vol. 91, 1994, 9871-9875.

Mercer-Smith, Janet A. et al., "The Development of Copper-67-Labeled Porphyrin-Antibody Conjugates", Targeted Diagnosis and Therapy vol. 1, 1988, 317-352.

Moan, J. et al., "A Change is the Qauntum Yield of Photoinactivation of Cells Observed During Photodynamic Treatment", Biological Abstracts, 86:7, 1988, Philadelphia, PA, US; Abstract No. 72079; Abstract p. AB-772 of Lasers Med. Sci., 3:2, 1988, 93-98.

Moan, J. et al., "Photosensitizing Efficiencies, Tumor and Cellular Uptake of Different Photosensitizing Drugs Relevant for Photodynamic Therapy of Cancer", Biological Abstracts, 85:5, 1988, Philadelphia, PA, US; Abstract No. 49732; Abstract p. AB-723 of Photochem. Photobiol., 46:5, 1987, 713-722.

Moan, J. et al., "The Mechanism of Photodynamic Inactivation of Human Cells in Vitro in the Presence of Haematoporphyrin", Biological Abstracts, 68:10, 1979, Philadelphia, PA, US; Abstract No. 62117; Abstract p. 6230, BR J. Cancer, 39:4, 1979, 398-407.

Montag, Anthony G. et al., "Karyometric Features in Nuclei Near Colonic Adenocarcinoma", Anal. Quant. Cytol. Histol. vol. 13, 1991, 159-167.

Musser, David A. et al., "The Binding of Tumor Localizing Porphyrins to a Fibrin Matrix and Their Effects Following Photoirradiation", Res. Comm. In Chem. Path. And Pharm. vol. 28, No. 3, 1980, 505-525.

Osaka, Tetsuya et al., "Transmission Electron Microscopic Study on Electroless Plated Nickel-Molybdenum-Phosphorus Alloy Film", Jpn. J. Apple Phys Part 1, vol. 28, Suppl. 28-3, 1989, 229-233.

Patel, K. B., "Fluorescing Cells in Sputum After Parenteral HPD", Porphyrin Localization and Treatment of Tumors, 1984, 521-530.

Pegaz, B. et al., "Effect of the Lipophilicyt on the Phtothrombic Activity of Biodegradable Nanoparticles Loaded with Porphyrin Derivatives", TNT2004 Segovia Spain, 2004, 1-2.

Rao, Polisetti D. et al., "Rational Syntheses of Porphyrins Bearing up to Four Different Meso Substituents", J. Org. Chem. vol. 65, No. 22, 2000, 7323-7334.

Roberts, Jeanette C. et al., "Preparation and Characterization of Copper-67 Porphyrin-Antibody Conjugates", Journal of Immun. Methods vol. 105, 1987, 153-164.

Roby, Tina J. et al., "Discriminant Analysis of Lower Respiratory Tract Components Associated with Cigarette Smoking, Based on Quantitative Sputum Cytology", Acta Cytol vol. 34, 1990, 147-154.

Roby, Tina J. et al., "Reliability of a Quantitative Interpretation of Sputum Cytology Slides", Acta Cytol vol. 34, 1990, 140-146.

Schumann, G. B. et al., "Quantitative Sputum Cytologic Findings in 109 Nonsmokers", Am Rev Respr Dis vol. 139, 1989, 601-603.

Shulok, Janine R. et al., "Subcellular Localization of Hematoporphyrin Derivative in Bladder Tumor Cells in Culture", Photochem and Photobiol vol. 51, No. 4, 1990, 451-457.

Sidransky, David, "Importance of Chromosome 9p Loss in Human Lung Cancer", J Natl Cancer Inst vol. 87, 1995, 1201-1202.

Tockman, Melvyn S. et al., "Sensitive and Specific Monoclonal Antibody Recognition of Human Lung Cancer Antigen on Preserved Sputum Cells: A New Approach to Early Lung Cancer Detection", J Clin Oncol vol. 11, 1988, 1685-1693.

Tockman, Melvyn S., "The Early Detection of Second Primary Lung Cancers by Sputum Immunostaining", Chest vol. 106, 1994, 385s-390s.

Wingo, Phyllis A. et al., "Cancer Statistics", CA Clinical J Clin vol. 45, 1995, 8-30.

\* cited by examiner

METHOD FOR DETERMINING PRESENCE OF CARCINOMIC CELLS WITH 5, 10, 15, 20-TETRAKIS (CARBOXYPHENYL) PORPHINE

RELATED APPLICATIONS

This application is a division application of U.S. patent application Ser. No. 13/158,595, entitled Method for Prognosing Response to Cancer Therapy with 5,10,15,20-Tetrakis (Carboxyphenyl) Porphine, filed on Jun. 13, 2011 and issued as U.S. Pat. No. 8,486,656 on Jul. 16, 2013, which is a divisional application of U.S. patent application Ser. No. 12/715,627, entitled Method for Prognosing Response to Cancer Therapy with 5,10,15,20-Tetrakis(Carboxyphenyl) Porphine, filed on Mar. 2, 2010, and issued as U.S. Pat. No. 7,960,138 on Jun. 14, 2011, which is a continuation application of U.S. patent application Ser. No. 12/133,855 entitled Method for Making 5,10,15,20-Tetrakis(Carboxyphenyl) Porphine (TCPP) Solution and Composition Comprising TCPP, filed Jun. 5, 2008, and issued as U.S. Pat. No. 7,670,799 on Mar. 2, 2010, which is a divisional application of U.S. patent application Ser. No. 10/933,140 entitled Method for Prognosing Response to Cancer Therapy with 5,10,15,20-Tetrakis(Carboxyphenyl) Porphine, filed Sep. 2, 2004 and issued as U.S. Pat. No. 7,384,764 on Jun. 10, 2008, which is a divisional application of U.S. patent application Ser. No. 09/989,092 entitled Compositions and Methods for Detecting Pre-Cancerous Conditions in Cell and Tissue Samples Using 5,10,15,20-Tetrakis(Carboxyphenyl) Porphine, filed Nov. 19, 2001, and issued as U.S. Pat. No. 6,838,248 on Jun. 4, 2005, which claims the benefit of U.S. Provisional Patent Application Ser. No. 60/249,505 entitled Method of Detecting Pre-Cancerous Conditions in Human Tissue Samples Using 5,10, 15,20-Tetrakis(Carboxyphenyl) Porphine, filed on Nov. 17, 2000, and the specification thereof of each is incorporated herein by reference.

FIELD OF THE INVENTION

This invention relates to the use of certain porphyrins to detect dysplastic, pre-cancerous, and cancerous cells from various tissue samples both in vitro and in situ.

BACKGROUND OF THE INVENTION

Various scientific and scholarly articles are referred to in parentheses throughout the specification. These articles are incorporated by reference herein to describe the state of the art to which this invention pertains.

Pathologists, who examine disease progression and analyze tissue samples for abnormalities, including cancer, have determined that a cellular condition called dysplasia, which refers to abnormal formation or maturation of cells, can potentially identify cells in a pre-cancerous condition. Unchecked, dysplasia can progress through mild, moderate and severe stages and eventually to cancer. About one in seven of the moderate cases of dysplasia will progress to cancer, and as many as 83% of cases with severe dysplasia have been reported to progress to cancer, depending on the types of cells involved. However, removal of mild and moderate dysplasias greatly reduces the development of cancer. In the lung, removal of dysplastic cells not only greatly reduces the formation of cancerous cells, but in some cases pulmonary tissue will return to a normal morphology.

In general, the earlier cancers are detected, the better the prognosis is for patient survival. If breast cancer is detected early when it is still localized to a single mass, the five-year survival rate is more than 96%. When it has spread to a distant location, the five-year survival rate is less than 20%. For lung cancer, when it is detected as a single mass the 5-year survival is more than 46%. When it has spread, the five-year survival is less than 14%. For cervical cancer, additional improvement in survival occurs when pre-cancerous changes are found and treated before developing into a more severe stage (Boring and Squires 1993, *CA Cancer J Clin* 43:7-26 and Ferguson 1990, *Hematol Oncol Clin N Am* 4:1053-1168).

Lung carcinoma is presently the leading cause of cancer mortality among men and women in the United States (Wingo et al. 1995, *CA Clinical J Clin* 45.8-30). In 1997, there were an estimated 160,000 deaths from lung cancer, accounting for 12% of all cancer deaths in U.S. men and 2% in U.S. women (Boring & Squires 1993, supra). Lung cancer is also one of the most lethal types of cancer, as reflected in a five-year survival rate of only 14%. The poor prognosis for lung cancer patients, relative to other types of human cancer, is due largely to the lack of effective early detection methods. At the time of clinical (symptomatic) presentation, over two thirds of all patients have regional nodule involvement or distant metastases, both of which are usually incurable. In studies of patients with localized (Stage 0 or 1) lung cancer, however, 5-year survival rates have ranged from 40% to 70% (Boring & Squires, 1993, supra; Ferguson, 1990, supra).

Historically, the only diagnostic tests used to detect lung cancer before symptoms occur have been sputum cytology and chest radiography. As a consequence, the efficacy of these tests as mass screening tools has been extensively evaluated in studies over the past several decades. Both tests detect presymptomatic, earlier-stage carcinoma, particularly carcinoma of squamous cells.

Improvements in screening methods have largely centered around improving the utility of sputum cytology through technologic advances in microscopy. Sputum cytology requires a visual examination of a cell sample during which cell size, shape, organization, and a ratio between the size of the cell's nucleus and cytoplasm is used to determine the cell's morphology. Because this assessment of cell morphology requires a visual inspection and classification, the technique requires a significant amount of expertise on behalf of the clinical observer. Various investigations have been conducted with results suggesting that computer-assisted, high resolution image analysis enables detection of subvisual changes in visually normal nuclei associated with several tissue types (Montag et al. 1991, *Anal Quant Cytol Histol* 13:159-167; Haroske et al. 1988, *Arch Geschwulstforsch*, 58:159-168; Hutchinson et al. 1992, *Anal Quant Cytol Estol* 4:330-334). Computer-assisted analysis of DNA distribution in cell samples provided 74% correct morphological classification of nuclei without human review of the material and without the need for visually abnormal nuclei being present when compared with standard cytological testing.

The morphologic assessment of cytological specimens has also improved due to advances in the understanding of lung tumor pathology. Much of this work has centered on the identification of "biomarkers." Biomarkers refer to a wide range of progressive phenotypic and genetic abnormalities of the respiratory mucosa which may be used in determining the potential for bronchial epithelium to fully transform into a malignant tumor. Markers have been broadly classified as morphological changes, immuno/histochemical markers for differentially expressed proteins, markers for genomic instability, markers of epigenetic change (e.g., abnormal methylation), and gene mutations (Hirsh et al. 1997, *Lung Cancer* 17:163-174).

The expression levels of these markers are now being evaluated in dysplastic and neoplastic cyto/histological tissue samples collected from high risk populations. Among those specimens currently being targeted for exploratory marker analysis is sputum. Interest in sputum samples for biomarker research has been generated from the long-held belief that exfoliated cells recovered in sputum may be the earliest possible indication of an incipient carcinoma, since lung cancer most frequently develops in the bronchial epithelium. Through application of sophisticated molecular genetic techniques (e.g., PCR-based assays), studies are providing evidence that selected biomarkers can be detected in sputum (Mao et al. 1994, *Cancer Res* 54:1634-1637; Mao et al. 1994, *Proc Natl Acad Sci USA* 91:9871-9875; Sidransky 1995, *J Natl Cancer Inst* 87:1201-1202; Tockman et al. 1988, J Clin Oncol, 11: 1685-1693; Tockman et al. 1994, *Chest*, 106:385s-390s).

Commercially available cancer screening or detection services rely on tests based on cytomorphological diagnosis by trained clinicians who look at each sample and determine the extent and identity of abnormal cell types. This process is not only expensive and time-consuming, it also introduces human judgment and therefore error into the procedure. Recently, a method has been developed for detecting cancerous cells of the lung through use of 5,10,15,20-tetrakis(carboxyphenyl)-porphine (TCPP) (U.S. Pat. No. 5,162,231 to Cole et al.) This method relies on the propensity of cancerous cells to accumulate TCPP from their environment in a greater amount than non-cancerous cells. Upon incubation of a cell sample for 6-24 hours with 200 ug/ml TCPP, the TCPP entered cells and bound to the perinuclear membrane and mitochondria of neoplastic cells. TCPP fluoresces under ultraviolet light, and cancerous cells may thereby be diagnosed solely by the intensity of fluorescence, without reference to morphology. The extension of the use of this compound to identifying pre-cancerous tissue conditions (e.g., dysplastic cells) would permit screening in high risk populations to identify those individuals whose tissues are progressing toward invasive cancer conditions, and thereby facilitate catching the cancer or dysplasia at the most treatable stage. The desirable characteristics of such a screening method would be a procedure that is rapid, inexpensive, and requires a minimum of technical expertise.

For the foregoing reasons, there is a need for a technique and methodology for detecting dysplastic cells in their earliest stages. In addition, there is a need for a technique that can provide highly reliable diagnostic results and that does not rely on the subjective analysis of the clinician performing the diagnosis.

SUMMARY OF THE INVENTION

The invention is derived from the discovery that TCPP can be used to detect dysplastic and precancerous as well as cancerous cells, in conjunction with a novel and more efficient method of solubilizing TCPP, improved staining procedures, and a variety of cell sorting strategies. TCPP is a fluorescent compound that has now been discovered to bind to components of live or fixed precancerous as well as cancerous cells in a manner that allows the state of the cells and the tissue from which they came to be categorized on a disease progression continuum. This method of detection of precancerous tissues is well-suited to in vitro diagnosis of tissue or cell samples as well as in situ diagnosis.

One aspect of the invention is a method for detecting precancerous cells, which in its simplest form comprises incubating live or fixed (i.e., killed) cells in a TCPP solution for sufficient time to bind to the cellular components, and detecting the bound TCPP with fluorimetry. This method has many variations. In one variation, the cells are fixed on a surface, preferably a microscope slide, and most preferably in a monolayer. In another variation, the cells are treated with formalin or another suitable fixative solution, maintained in suspension, treated with TCPP, the cells separated from the unbound TCPP, and then analyzed and sorted by flow cytometry.

Preferred embodiments of the incubation step include using a TCPP solution with about 4 µg/mL to 400 µg/mL TCPP, a temperature between about 23° C. and about 42° C., and a time between about 0.2 minutes to 2 hours. Unbound TCPP is removed and the remaining TCPP is detected fluorimetrically. In a preferred embodiment, the TCPP is detected between about 1 and 24 hours after the assay is performed.

In another embodiment of the invention, the percentage of fluorescent cells in a cell sample is calculated. Preferred embodiments comprise analysis of fluorescent cells for their fluorescence intensity and other cytomorphological features. In a particularly preferred embodiment, fluorescent cells are classified according to a set of pre-determined fluorescence intensity and cytomorphological features, which facilitates characterization of the cells along a continuum ranging from normal to metaplastic to dysplastic (mildly to severely) to carcinomic (mildly to severely), and increases the efficiency and reliability of the diagnoses and prognoses made using the methods of the invention. Other embodiments of the invention comprise separating the normal or metaplastic cells in a sample from the dysplastic or carcinomic cells, using criteria of fluorescence intensity (e.g., via fluorometric flow cytometry).

In order to facilitate practice of the aforementioned detection method, another aspect of the present invention provides a method for making a TCPP solution comprising dissolving TCPP in about 50% to about 90% alcohol at a pH greater than about pH 8.5 and less than about pH 12.5. In one preferred embodiment, the alcohol is isopropanol, and in another preferred embodiment the pH of the solution is adjusted with sodium bicarbonate or ammonium hydroxide.

Another aspect of the invention is a composition that comprises TCPP in about 50% to about 90% alcohol at a pH greater than about pH 8.5 and less than about pH 12. In one preferred embodiment, the alcohol is isopropanol, and in another preferred embodiment the pH of the solution is adjusted with sodium bicarbonate or ammonium hydroxide. In one embodiment, the composition is made by the method for making a TCPP solution. In a related embodiment, the TCPP solution used in the detection method is diluted.

In another aspect of the invention, cells are in situ within a mammalian patient. Cells are exposed to TCPP solution and fluorescence is detected by using endoscopic techniques.

Another aspect of the invention is a kit for detecting precancerous cells, which comprises the composition of the invention in a container. In another embodiment, the kit comprises one or more additional components, such as instructions and reagents for carrying out the detection method of the invention, or positive and negative controls.

Other features and advantages of the present invention will be better understood by reference to the drawings, detailed description and examples that follow.

DETAILED DESCRIPTION OF THE INVENTION

The present invention comprises compositions and methods for detecting precancerous conditions in human cells using 5,10,15,20-tetrakis(carboxyphenyl)porphine (TCPP). The present invention derives from the discovery that TCPP binds specifically to precancerous abnormal cells in addition to cancerous cells, but does not bind to normal (noncancerous) cells. Moreover, this differential binding is observed in fixed cells as well as live cells. In addition to this new and useful property of TCPP, the invention additionally incorporates an improved method for solubilizing TCPP that preserves its activity to a greater extent, as well as several novel aspects that make the method better suited to screening and automation. Using the methods of the invention, less time is required for the cells to bind the TCPP when compared with the method described in U.S. Pat. No. 5,162,231 (e.g; 0.2 min-2 hours versus 24 hours), and a lower concentration of TCPP (e.g., 40 µg/mL versus 200 µg/mL) is also required. In addition, a monolayer of cells may be used rather than a solution of cells, though a solution of cells may also be used.

Key to the convenience and efficiency of the detection method is the novel method of solubilizing the TCPP. Previous methods used 1 M NaOH to dissolve the porphyrin. That method required titration with 1M HCl, which is inaccurate, and required that each solution be checked for undissolved TCPP. Additionally, the NaOH method placed the porphyrin in an oxidizing environment with pH as high as 13.0, thereby exposing the porphyrin to a high risk of degradation. The solubilization method of the present invention uses pH 9.1 in conjunction with the novel addition of 90% alcohol to effect a more complete and reliable solubilization. Finally, the method of this invention uses a buffer to stabilize the pH of the final working TCPP solution in the preferred range of 5.8 to 6.8.

The invention involves the detection of precancerous and cancerous cells in samples of human tissues using the unique propensity of these cells to bind TCPP in a greater amount than healthy cells. As used herein, the terms "precancerous" or "abnormal precancerous" refer to cells that exhibit mild to severe dysplasia, and the term "cancerous" refers to cells that exhibit mild to severe carcinoma. These cytological states are morphologically defined herein by the criteria used to determine cell morphology using Papanicalou-stained ("PAP-stain") cytology. They also may be defined by other indicators commonly used in the art for a particular cell or tissue (e.g., indicators of pulmonary inflammation in lung or sputum samples). From "normal" to "severely carcinomic," the states of a cell are classified herein as (1) normal (no significant abnormalities), (2) metaplasia (squamous metaplasia), (3) mild dysplasia (squamous atypia), (4) moderate dysplasia (squamous atypia), (5) severe dysplasia (marked squamous atypia), (6) carcinoma in situ squamous (CIS, non-invasive) (also referred to as mild to moderate carcinoma), and (7) squamous cell carcinoma (well-differentiating keratinizing type-invasive) (also referred to as moderate to severe carcinoma). It has been determined in accordance with the invention that following exposure to TCPP, dysplastic and carcinomic cells display TCPP fluorescence, while normal cells display little or no TCPP fluorescence. Some metaplastic cells may display low to moderate TCPP fluorescence, but in many instances they do not; hence TCPP fluorescence is not as reliable an indicator for metaplasia as it is for dysplasia and carcinoma.

The method comprises (1) incubating a sample of fixed or living cells with TCPP for a time sufficient to allow TCPP to bind to cellular components of abnormal precancerous or cancerous cells, if any are present in the sample, (2) removing unincorporated TCPP, (3) determining by fluorimetry the amount of TCPP remaining in the sample, if any; and, optionally, depending on the results of step (3), (4) evaluating TCPP fluorescing cells for their state of divergence toward cancer from the normal (or abnormal metaplastic, but not dysplastic), state. Specifically, as described above, the method of the invention enables a determination that a cell sample contains cells which are dysplastic (mildly to severely) or carcinomic (mildly to severely).

In an exemplary, but non-limiting embodiment, the detection method comprises the following steps:
1. fixing cells in a monolayer on a microscope slide;
2. exposing cells to TCPP solution at about 40 µg/mL in a buffered solution at about pH 6.1 (e.g., by dipping slides into the solution or by placing drops of solution onto the slides) at about 36° C. for a specified time, as described below;
3. washing slides with a buffered solution at about pH 6.1;
4. waiting at least 1 hour but not more than 24 hours; and
5. quantitating fluorescence from cells at about 610-740 nm when excited with about 380-450 nm light.

Variations of this exemplary method are set forth in greater detail below.

When used herein in describing components of assay mixtures or other parameters of the invention, the term "about" means within a margin of commonly acceptable error for the determination being made, using standard methods.

The first step, incubating the cells with fixative, is optional, but preferred, inasmuch as it has been found to reduce the time required for incubation, as well as the TCPP concentration in the working solution, in this exemplary embodiment and in others.

The sections below set forth a variety of other embodiments of the present invention.

The methods of the invention may be used on a variety of cell types as described below and further are applicable to veterinary as well as human diagnostic and prognostic applications. Accordingly, the term "patient" or "subject" as used herein is intended to apply to a human or an animal.

The detection method may be used to detect precancerous and cancerous cells in cell samples in vitro. Cell samples may be acquired by any of the methods currently used in the field of cytopathology. For example, cells may be collected from sputum samples (see Example 1), cervical swabs, bronchial washings, fine needle aspiration and core biopsies of thyroid and breast, bladder washings, urine, mouth washing, enemas, and other biopsies known in the art. Other sources of cell samples include blood or fractions thereof, lymph, cerebrospinal fluid, bone and bone marrow, to name a few. The method of the invention is applicable to any cell sample from any tissue or organ in the body.

Optionally, the cells may be fixed by standard procedures before exposure to TCPP, including but not limited to solutions containing formaldehyde, methanol, ethanol, or isopropanol. In one embodiment, the cells are fixed in 95% ethanol.

The assay may be performed in solution by measuring total fluorescence per cell density, or by adhering the cells onto a surface. Cells need not be treated with a fixative, but fixing cells is preferred in some embodiments, particularly those in which the cells are adhered to a solid support. In one embodiment, the cells are adhered as a monolayer to a slide. In other embodiments, the liquid-based slide preparation system MonoPrep2 or MonoPrepG (MonoGen, Inc., Herndon, Va.) or the Thinprep Processor (Cytyc Corporation, Marlborough, Mass.) is used.

The method of the invention may also be used to detect precancerous and cancerous cells in situ as well as an aid in resective surgery. For example, the method may be used to detect dysplastic cells in the lung in situ by injection of TCPP in a suitable medium followed by fluorescence bronchoscopy. A similar method may also be used to detect abnormal cells for excision during surgery. In situ applications may be found for any of the organs of the body, including, but not limited to, breast, prostate, lungs, cervix, throat, bladder, oropharynx, skin, and gastrointestinal tract by use of a similar endoscopic device. The amount of TCPP preferred for use in this embodiment is determined by the mode of administration and the site of delivery. For instance, if TCPP is injected into the bloodstream, the effective concentration of TCPP will depend on its maximum solubility in saline or blood (e.g., about 100 μg/mL). For injection directly into affected tissue, an effective amount of TCPP will depend on the target tissue and the proximity of the injection to that tissue (e.g., about 1-20 mg). In lung, an aerosol delivery of, e.g., 5-10 ml at a concentration of 20-50 μg/mL should be suitable. Methods of determining such amounts of TCPP to be administered as a diagnostic agent are well known to medicinal chemists and others of skill in the relevant art.

The TCPP concentration in the working solution and the duration of time the cells are exposed to TCPP solution are two variables that may be altered in a coordinated manner. The TCPP concentration is preferably 4-100 μg/mL, more preferably 4-40 μg/mL, and most preferably 20-40 μg/mL. The time of exposure may vary from about 0.2 minute to about 2 hours in one embodiment, and 10 to 60 minutes in a more preferred embodiment. When low concentrations of TCPP solution are used, a longer exposure time is appropriate, and when high concentrations of TCPP are used, a shorter exposure time is appropriate. For instance, in preferred embodiments, slides are exposed for 10 minutes in 40 μg/mL TCPP, and alternatively for 60 minutes in 4 μg/mL TCPP. The method to optimize the concentration of TCPP in the working solution and time of exposure are well known to those skilled in the art of cytology, the goal being to achieve the highest specific binding of TCPP to the cellular components while minimizing the background and other non-specific uptake and fluorescence.

The TCPP solution is comprised of TCPP in a buffered aqueous medium at about 36° C. In one embodiment, the buffering capacity is due to 100 nM MES; however, a concentration range of 20 to 200 mM can be used in the method with equal efficacy. In one embodiment, the solution has a pH of about 6.1; however, a pH range from 5.8 to 6.7 may be used with sufficient efficacy. Other buffering compounds that are effective in the range of pH 5.8-6.7 may also be used. While the exposure step is not particularly sensitive to temperature, a temperature somewhat above room temperature is desirable for optimization. The suitable temperature range for the exposure step is about 23° C. to about 42° C. in a preferred embodiment and about 30° C. to about 40° C. in a more preferred embodiment.

Other compounds may be added to the working solution to reduce background fluorescence, increase stability, or reduce autofluorescence or quenching. For example, detergents may be used to lower background fluorescence and reductants, antioxidants, and other inhibitors of the generation or diffusion of active oxygen species may be used to prevent oxidation of the TCPP or reduce photobleaching. Compounds of interest include, but are not limited to, polyethlyne glycols, tritons, dithiothreitol, dithiocrithritot, 2-mercaptoethanol, or the "Antifade kits" supplied by Molecular Probes, Inc. (Eugene, Oreg., P-7481, S-2928, S-7461). In addition, hematoxylin may be included with the TCPP, to act as a counterstain and facilitate white light microscopy.

The wash solution is generally similar to the aqueous solution used for the TCPP working solution but without the TCPP. If microscope slides are used, the slides should be washed at least once, most preferably three times, and preferably with agitation in excess wash solution. If the assay is done in solution, unbound TCPP may be removed by centrifuging the cells, decanting the supernatant and resuspending the cells in fresh buffer. This step may be repeated if necessary. Alternative means of separating cells from staining solution may also be used, such as filtration with capture of cells on a membrane or rapid dialysis (including spin dialysis). The proper conditions of the wash may be determined by monitoring the fluorescence of the cells. The wash should be sufficient to remove background and other non-specific binding, but not so excessive as to remove specifically bound TCPP from the cellular components. The optimization of the wash step is well known to those in the art of cytology. Compositions that may be added to the wash solution to improve efficacy or stability include, but are not limited to, alcohols, detergents or low molarity salt solutions.

An important step in the detection method is to allow more than 1 hour but less than 24 hours between the time the slide has been exposed to the TCPP working solution to the time the slide is read. When the slide is read after 24 hours, there may be too much deterioration in the TCPP to yield an accurate result. When cells are read before 1 hour, the level of background fluorescence may be excessively high.

The wavelengths used for the detection step are encompassed by broad ranges in which specific peak ranges will be most efficient. The peak of excitation of TCPP in an aqueous solution of pH 5.0-7.0 occurs at about 415 nm, while one peak of emission occurs at about 645 nm and a secondary peak of emission occurs at about 706 nm. In general, TCPP may be detected by illuminating the sample with ultraviolet (UV) light and detecting the light emitted from the sample above about 500 nm. The wavelengths used to excite TCPP in the method of the invention may preferably encompass part or all of the range from about 380 to about 450 nm, and most preferably a narrow band of wavelengths near about 415 nm. Likewise, the wavelengths detected may encompass part or all of the range from about 610 nm to about 740 nm and most preferably a narrow range near about 650 nm. Under certain circumstances obvious to those skilled in the art of fluorescence microscopy, it may be preferable to detect emissions in a narrow range near about 706 nm. The selection of wavelength can most easily be accomplished by optical filters. Filter sets for popular fluorescent dyes are readily available from Molecular Probes (Eugene, Oreg.), for example. The appropriate wavelength selection to excite and detect TCPP in the method of the invention may most easily be obtained by using a filter set designed for detecting fluorescein isothiocyanate (hereinafter "FITC"), which generally has an excitation filter of 400 to 490 nm and a barrier filter for emission above 500 nm. The selection of other filter systems is well known to those skilled in the art of microscopy.

Fluorescence may be detected visually or mechanically, manually or by automated means. Cells having even moderate fluorescence as compared to non-fluorescing cells are easily distinguishable by the human eye. Hence, certain embodiments of the invention comprise simply viewing TCPP-treated cells under a fluorescence microscope and quantitating the percentage of fluorescing cells in the sample manually. However, preferred embodiments comprise automated methods well known in the art, and mechanical quantitation wherein a cell is "counted" as fluorescent if it displays fluorescence over a pre-determined threshold level programmed into the counting device, as is well known in the art. For instance, in embodiments comprising a monolayer of cells adhered to a microscope slide, an automated slide reader can be programmed to count as fluorescent any cell having fluorescence pre-determined to be of statistical significance compared to an equivalent, normal cell, as determined by standard statistical methods (such devices also may be programmed to count cells of a certain shape, which can supply a second indicator of precancerous or cancerous abnormality). Alternatively, for embodiments comprising a solution-based assay, TCPP-stained and washed cell samples may be analyzed by fluorescence-activated cell-sorting (FACS), wherein the FACS is programmed to separate cells having a pre-determined level of fluorescence, as may be determined statistically by comparison with normal cells.

The total number of cells present in a sample is determined in order to calculate a percentage of that total that are TCPP-fluorescent. This determination may be accomplished in a variety of ways known in the art. In one embodiment all cells are stained with hematoxylin and counted under white light microscopy. In another embodiment, the cells are stained with a suitable fluorescent counter stain (e.g., one that stains the external or internal membranes of a cell) that fluoresces at a different wavelength from TCPP. In this latter embodiment, the ratio of TCPP fluorescence to cell marker fluorescence is quantitated.

As mentioned, the novelty of the methods of the invention resides in the inventors appreciation that TCPP staining identifies not only cancerous cells, as previously known, but also identifies precancerous dysplastic cells. Because of this, the above-described method yields vastly more information than previously believed possible. Accordingly, the results of the TCPP fluorescence quantitation will be determinative of whether subsequent analytical steps are taken, and in what form.

For instance, the method will identify a percentage of cells in a sample that are TCPP fluorescent. If about 1-3%, more particularly about 2-3%, of the cells in a sample are fluorescent, then sample contains cells that are at least abnormal precancerous (dysplastic) or cancerous. Accordingly, a simple analytical scheme involves determining if a sample contains at least about 1% TCPP-fluorescent cells. If it does not, the sample is diagnosed as negative (normal). If it does, further testing is recommended for the patient. It should be noted in connection with this embodiment that, even if a sample contains fewer than 1% fluorescent cells, other factors (e.g., pre-disposition of the patient to cancer, or a pre-existing cancer in another tissue) may suggest that further testing be performed. One advantage of the invention that is described in greater detail below is that an enriched population of fluorescent cells may be obtained from the patient via FACS.

In addition, the level of fluorescence of a given cell in a sample has been found to correlate with the cancer-associated state of that cell (see Example 1). Accordingly, individual cells or groups of cells may be evaluated for their overall fluorescence intensity, and a determination of whether further testing is required may be based in part on this evaluation.

The terms, "high", "medium" and "low" fluorescence and related terms as used herein, will be understood by one of skill in the art to be comparative terms wherein the fluorescence intensity of a single cell or group of cells in a test sample is compared at least with cells from an equivalent source (e.g., sputum) known to be normal with respect to cancer (negative control). This comparison may be accomplished by visual estimation, or, in automated systems, it may be programmed using statistical parameters such as variation from the median fluorescence of a sample population, as described in Example 2. In preferred embodiments, cells from a test sample are compared for fluorescence intensity with additional control cells whose cancerous state has been pre-determined and pre-correlated with a TCPP fluorescence intensity (for instance, as described in Example 1).

The terms "fluorescent" and "non-fluorescent" are also used herein. In keeping with the above-discussed definitions of various levels of fluorescence intensity, the terms "non-fluorescent" and "fluorescent" are used as comparative terms, wherein fluorescence is compared against normal cells from an equivalent source, and/or against general background fluorescence arising from the reagents or equipment used in detecting the fluorescence. Hence, if a cell or cell sample is determined "fluorescent," then fluorescence is present at some intensity above background fluorescence of fluorescence observed in known normal cells. If a cell or cell sample is determined "non-fluorescent," then the fluorescence observed is minimally or not at all in excess of background fluorescence or fluorescence observed in normal cells. This comparison would be understood by one of skill in the relevant art.

A cytomorphological evaluation combined with TCPP fluorescence is particularly useful with cell cultures that have a low level of fluorescence because a visual evaluation of the cells with standard evaluation techniques can easily differentiate the slightly fluorescing metaplastic (non-cancerous) cell from dysplastic (precancerous) cells. One embodiment of the method comprises an additional step of cytomorphological evaluation in addition to quantitation of fluorescence, especially using a standard cytological stain such as haematoxylin to help visualize cell and nuclear outlines. Another embodiment employs cytomorphological evaluation as a subsequent step, if certain threshold requirements are met, e.g., the sample contains more than 1% fluorescent cells.

In a particularly preferred embodiment of the invention, selected cytomorphological features are combined with fluorescence intensity to produce a classification system that is very useful for efficient, reproducible diagnosis of the various stages of metaplasia, dysplasia and carcinoma that may be present in a cell sample. Such a classification system is described in detail in Example 1. In this embodiment, TCPP-fluorescent cells are assigned one or more numerical classes, based on fluorescence intensity and simple morphological features including cell shape and size, number or size of nuclei, presence of cell clusters and degeneration of cells or cell clusters, presence of irregular anisoid cells, visibility of cell membrane, and presence and nature of nuclear debris. The technician or scientist performing the cytomorphological evaluation of TCPP-fluorescing cells can use the classification as a checklist, i.e., a cell being examined may be checked off as "plus" or "minus" with respect to each of the numerical classes. The number of numerical classes assigned to a particular cell and the pattern of specific classes assigned to a cell are both informative as to the cancerous or precancerous condition of that cell. By way of illustration, Example 1 sets forth a classification system comprising 14 numerical classes. As shown in Table 2 of that example, which assays presents of sputum samples, negative or metaplastic cells generally are assignable to few of the classes, while severely carcinomic cells are assignable to several. As further illustration, negative or metaplastic cells are frequently assigned class 11, while moderately dysplastic to carcinomic cells are not, and carcinomic cells are frequently assigned class 6, while normal, metaplastic and dysplastic cells are not.

In another embodiment of the invention, TCPP-treated cells in solution from a single patient determined to have carcinoma can be separated by flow cytometry based on their level of fluorescence. Cells showing a higher level of fluorescence are considered to be cancerous while cells with moderate to low levels of fluorescence are considered dysplastic, and cells with no fluorescence are considered to be normal. This type of separation enables a patient's dysplastic or cancerous cells to be compared against the patient's own normal cells, thereby providing an ideal "internal" control population.

In another embodiment, by separating cancerous and normal cells from the same patient, various chemotherapeutic agents can be assayed to test for effectiveness. Separated cells are dispensed into aliquots. A selected therapeutic agent can then be mixed at the same concentration with an aliquot of highly fluorescent cells and an aliquot of low level fluorescent cells. This step can be repeated with fresh aliquots and a different therapeutic agent. Cell death rates can be assessed using techniques known in the art. The most preferred therapeutic agent for treatment can then be determined by choosing the chemo-therapeutic agent that killed the highest number of cells determined to be cancerous (i.e., highly fluorescent cells) and killed the fewest number of normal cells (i.e., cells with little or no fluorescence after TCPP treatment).

In conjunction with the screening or diagnostic detection method of the invention, a method for dissolving TCPP for use in the method as well as other applications has been developed. This method comprises dissolving TCPP in about 50% to about 90% alcohol with a pH greater than about pH 8.5 and less than about pH 12.5. Preferred for use in the invention are lower alcohols such as methanol, ethanol, isopropanol and n-propanol. More preferably, the alcohol is isopropanol and its pH is adjusted with sodium bicarbonate or ammonium hydroxide to a pH greater than 8.5 and less than 10.0. The concentration of isopropanol may be from 50% to 90% and the sodium bicarbonate may be from 20 mM to 100 mM in some embodiments. The concentration of TCPP may be up to about 2 mg/mL. In one embodiment, the TCPP is dissolved at 1 mg/mL in a solution of 50% isopropanol 50 mM sodium bicarbonate.

The invention also comprises a composition useful for use in any method utilizing TCPP that comprises TCPP in alcohol with a pH greater than 7. This solution would preferably be made by the method for dissolving TCPP detailed above. This composition should preferably be stored at about 4° C. in the dark.

The invention additionally encompasses kits for the detection of precancerous and cancerous cells comprising TCPP in a container, optionally with instructions. In one embodiment, the kit is designed to be used with the detection method of the invention. In one embodiment, the kit includes the composition of the invention comprising TCPP solubilized in basified alcohol in a container. This TCPP solution may be used as a stock solution which would be diluted into a buffered aqueous solution for the purpose of detecting precancerous and cancerous cells. The kit may contain the components for collecting the cell sample, as in the sputum collection container of Example 1, or alternately may contain items for the detection of precancerous cells in samples already acquired. The kit may be tailored for use with slide preparation systems, e.g., MonoPrep2 or MonoPrepG (Monogen, Inc., Herndon Va.) or the Thinprep Processor (Cytyc Corporation, Marlborough, Mass.), to name three. These kits may also be designed to be used with formats other than microscope slides, such as microtiter plates or flow cytometry devices. In any of the foregoing embodiments, the kit may comprise positive or negative controls, or both, as would be employed by one of skill in the art in conducting the assays of the invention.

The following examples are provided to describe the invention in greater detail. They are intended to illustrate, not to limit, the invention.

EXAMPLE 1

Glass Slide Assay for Detection of Pre-Cancerous and Cancerous Cells with TCPP

This example compares the diagnostic results achieved through standard cytomorphologic analysis of PAP-stained sputum slides versus slides treated with TCPP and analyzed by fluorescence microscopy. The results indicate that the TCPP detection technique of this invention is equivalent to conventional sputum cytology in the detection of neoplastic cells (dysplasia and carcinoma in situ) and frank carcinomas. The results also indicate that one skilled in the art can use the method, in conjunction with simple classification rules, to estimate the degree of dysplasia present in a tissue sample.

Methods

Sputum Processing Procedures Used in Production of Monolayer Slides.

All monolayer slides selected for analysis in this study were produced from sputum samples collected through patients performing the early morning, spontaneous cough technique. Specifically, patients were instructed to expectorate whatever material they coughed up across three consecutive mornings into a container filled with fixative consisting of 2% Carbowax in 50% alcohol/50% Saccomanno fluid with 0.03-0.05 mg/mL rifampin. Rifampin was added to the fixative solution to serve as a prophylactic against patients harboring *M. tuberculosis* or those patients who may be asymptomatic carriers of *N. meningitis*.

The 2% Carbowax solution was prepared by adding 2 mL melted Carbowax (150) to 98 mL of 50% ethanol and mixing for 30 minutes. Glassware used to make solution was kept warm to prevent hardening of wax on the surface during preparation, which can cause inaccurate measurement. Carbowax was removed before exposure to the TCPP working solution by immersion in 95% alcohol for at least 15 minutes.

Rifampin solution (3 mg/mL) was made by dissolving 300 mg capsules of rifampin into 100 mL ethyl alcohol and blending at high speed in a Waring blender. One mL of this solution was added to each 30 mL of Saccomanno solution or 20 mL per liter of Saccomanno solution and mixed thoroughly. The preparation of Saccomanno solution was according to standard methods well known to those in the art of cytology.

Two thin-prep microscope slides (Cytyc Corporation, Marlborough, Mass.) and a 50 mL plastic centrifuge tube were labeled with patient information. The sputum specimen was poured into a 50 mL plastic centrifuge tube and additional 50% ethyl alcohol solution added to bring the volume to 50 mL if necessary. The contents of the centrifuge tube were poured into a 250 mL Eberbach semi-microblender container and homogenized for 10 to 60 seconds, depending upon visual examination of the specimen and mucoid content. Thick mucoid specimens sometimes required longer blending times. The specimen was poured back into the centrifuge tube and centrifuged at 1850 rpm for 10 minutes. The supernatant was decanted, leaving 1 to 2 mL in the centrifuge tube to admix with the sediment (centrifugate). The tube was agitated on a vortex mixer for approximately 10 seconds. One to three drops of the sediment was placed into a PreservCyt vial (Cytyc Corporation, Marlborough, Mass.). The specimen was incubated for 5 minutes to deactivate all microbial and viral organisms.

Monocellular layers of the samples were fixed onto slides using the ThinPrep Processor (Cytyc Corporation, Marlborough, Mass.) according to the manufacturer's instructions. In the ThinPrep Processor, cells were collected onto a polycarbonate filter (pore size 0.5 mm) and transferred to a glass slide. The ThinPrep Processor then immediately deposited the slide into a fixative bath containing 95% ethanol.

TCPP Stock Solution.

400 mg of sodium bicarbonate was added to approximately 90 mL of the 50% isopropanol (50 mM sodium bicarbonate) and mixed until completely dissolved to make basified 50% isopropanol. One hundred milligrams of TCPP were slowly added to the basified 50% isopropanol (50 mM sodium bicarbonate) and mixed for 3 to 5 minutes until dissolved. The TCPP solution was brought to 100 mL volumetrically with the basified 50% isopropanol, mixed well and stored in an amber reagent bottle covered in foil in a refrigerated area. The final concentration of TCPP in the stock solution was 1 mg/mL.

TCPP Working Solution.

Fresh TCCP working solution was prepared each day. Approximately 10 mL of TCPP Stock Solution with concentration 1 mg/mL was brought to room temperature. Eight milliliters of the TCPP Stock Solution (1 mg/mL) were placed in a 200 mL volumetric flask and approximately 100 mL of the MES buffer was slowly added. The solution was gently mixed. Additional MES buffer was added to bring the solution to 200 mL volumetrically. The solution was mixed for 3 to 5 minutes and stored at 2-4° C. in an amber bottle. The final concentration of TCPP in the working solution was 40 µg/mL.

TCPP Exposure Procedure.

Slides were fixed in 95% alcohol for 30 minutes at room temperature. The slides were exposed to TCPP immediately after fixing or up to 3 days later. The slides were immersed in 40 µg/mL TCPP solution for 10 minutes at 36° C., then washed in 100 mM MES buffer three times, one minute each, at room temperature with agitation. Slides were viewed more than 1 hour but not more than 24 hours later.

Microscope Information.

The microscope utilized for observation of the TCPP treated sputum cell slides was an Olympus model BH-1 microscope with a sub-stage illuminator and above-stage mercury lamp for reflected light fluorescence microscopy. The mercury lamp has primary emission lines at 365 nm, 405 nm, 436 nm, and 545 mm. The fluorescence filter assembly consisted of two dichrotic cubes. The green cube (490 nm) contained a filter system with an excitation filter passing 400-490 nm and a barrier filter passing emission above 500 nm.

Sputum Slide Staining Procedures by Modified PAP-Staining Technique.

Procedure sequence (no.), reagent and time (min.:sec.) were as follows: (1) 95% alcohol 15:00; (2) tap water 1:00; (3) gil-i hemotox 2:30; (4) tap water 1:00; (5) bluing reagent: 30; (6) tap water 1:00; (7) 95% alcohol: 10; (8) og-6 1:30; (9) 95% alcohol: 10; (10) 95% alcohol: 10; (11) ea-50 1:15; (12) 95% alcohol: 20; (13) 95% alcohol: 30; (14) 100% alcohol 1:00; (15) 100% alcohol 1:00; (16) 100%-alcohol 1:30; (17) xylene 1:00; (18) xylene 1:00; and (19) xylene 1:00.

Methods for Routine Cytopathological Analysis of Papanicolaou-Stained Slides.

PAP-stained slides underwent semi-quantitative cytomorphological evaluation. (1) dysplastic and neoplastic cells were identified through use of traditional morphologic criteria, and (2) the expression levels of seven fundamental indicators of pulmonary inflammation (alveolar macrophages, neutrophils, columnar cells, mucus, mucous spirals, pigmented macrophages, metaplastic cells) were quantified. The methodology for quantifying these inflammation indicators have been previously discussed in the literature (Roby et al., 1989, *Acta Cytol* 34:147-154; Roby et al., 1990, *Acta Cytol* 34:140-146; Schumann et al., 1989, *Am Rev Respr Dis* 139: 601-603). The criteria used to determine cell morphology using PAP-stained cytology are discussed below.

No Significant Abnormalities.

Cells were identified as having no significant abnormalities if the following criteria were satisfied:
1. basophilic, ciliated epithelial cells admixed with macrophages with grade 1-2 pigment along with inflammatory cells;
2. round nuclei of epithelium basally oriented;
3. evenly dispersed chromatin;
4. inconspicuous nuclear membranes;
5. inconspicuous nucleoli; and
6. no metaplastic and no dysplastic cells present.

Squamous Metaplasia (without Dysplasia).

Cells were identified as squamous metaplastic without dysplasia if the following criteria were satisfied:
1. clumps of basophilic cells without cilia;
2. uniform cell and nuclear size;
3. low nucleus/cytoplasm (N/C) ratio;
4. nuclear chromatin finely granular; and
5. small rounded nucleoli (usually single) may be present.

Mild Dysplasia (Squamous Atypia).

Cells were identified as mildly dysplastic if the following criteria were satisfied:
1. smaller than metaplastic cells;
2. seen in cohesive clusters, or singularly;
3. cells lie flat (sheets) both nuclei and cytoplasm in focus;
4. cells vary slightly in size;
5. cytoplasm may be eosinophilic or basophilic;
6. cytoplasmic borders sharp;
7. nuclei vary slightly in size, usually round to oval, if divided 2 halves of nucleus are mirror images, N/C ratio may vary slightly;
8. nuclear membrane smooth;
9. nuclear chromatin (slightly increased) finely granular, occasional chromocenter; and
10. fiber cells, elongated cells with stretched cytoplasm and nucleus distinct nuclear membrane—fine reticular to granular cytoplasm usually bright yellow orange—keratinizing single, may form whorls around central core of keratin to make epithelial pearls.

Moderate Dysplasia (Squamous Atypia).

Cells were identified as moderately dysplastic if the following criteria were satisfied:
1. variation in size, usually larger but may be smaller than mild dysplasia;
2. more variation in shape and N/C ratio than mild dysplasia;
3. cytoplasm dense, acidophilia predominates; increased number of atypical cells;
4. nucleus may have unequal halves (not mirror images);
5. nuclear lobulations, crevices, and nodules are present; and
6. nuclear material may show hyperchromasia with more stippled-like chromatin pattern.

Severe Dysplasia (Marked Squamous Atypia).

Cells were identified as severely dysplastic if the following criteria were satisfied:
1. cells vary markedly in size and shape;
2. usually slightly larger cell size than moderate dysplasia;
3. N/C ratio is high but variable (with extremes);
4. single cells predominate; nucleus is more central than CIS;
5. nucleus may follow shape of cytoplasm; nucleus shows less distortion than CIS;

6. nuclear pleomorphism is increased with coarse chromatin present and condensation along nuclear envelope;
7. parachromatin, large nucleus, multi-nuclustered nuclear membrane focally thickened; and
8. cells show predominant acidophilic cytoplasm.

Carcinoma In-Situ Squamous (CIS, Non-Invasive).

Cells were identified as being carcinoma in situ squamous if the following criteria were satisfied:
1. cells single or in aggregates (clumps);
2. cell size variable—may be smaller or larger than marked dysplasia cells usually smaller than invasive squamous cell carcinoma;
3. cells are large, rounded with symmetrically located nucleus;
4. cell degeneration may be present;
5. scant cytoplasm, distributed uniformly may be keratinized or non-keratinized concentrically around the nucleus, (orangiophilic or basophilic);
6. N/C ratio variable—higher or lower than normal;
7. coarse dense nuclear chromatin granules may be interrupted by clear zones;
8. uniformly thickened chromatinic rim with undulation of nuclear membrane;
9. lobulations of nuclei may be seen;
10. cannibalism may be seen, but is unusual;
11. multinucleated cells may be present;
12. no nucleoli in nucleus; a mitotic cell may be present; and
13. clean background.

Squamous Cell Carcinoma (Well Differentiated Keratinizing Type-Invasive).

Cells were identified as squamous cell carcinoma if the following criteria were satisfied:
1. cells usually single, orangeophilic, but may be in clusters, and degenerate;
2. cells large or small, angular, with well preserved nuclei and distinct cell borders;
3. cells usually larger than in-situ, and may be pleomorphic, wide range of both size and shape;
4. pearl formation may be seen (cancer pearl);
5. moderate amount of cytoplasm with abnormal "tailing" (consistent with invasion); bizarre cell shapes—tadpole, star, spindle; a nuclear chromatin angular, with unpredictable clumping with hyperchromasia and parachromatin clearing and clearly defined chromatin, parachromatin interface;
6. chromatin is coarsely clumped, especially along the nuclear membrane;
7. nucleoli are large and acidophilic, if present;
8. nuclear membrane itself may be thickened and irregular; irregularity of thickness of nuclear chromatin rim;
9. N/C ratio is very high;
10. marked nucleolar irregularity in shape, size, numbers (daughter nucleoli); abnormal mitoses, multi nucleation;
11. cannibalism and multinucleation is common; and
12. necrotic background material is common.

Results

In a blinded study in which 60 samples were examined, the results indicate that abnormal cells (mild, moderate or severe dysplasia or cancerous) can be accurately detected with the TCPP detection procedure compared with the PAP-staining procedure (Table 1). If 2-3% of the TCPP-exposed cells were fluorescing, then the sample reliably correlated with at least the mildly dysplastic diagnosis. Fifty out of fifty sputum samples determined by the standard cytomorphological PAP-staining procedure to be mildly dysplastic to cancerous were also identified as abnormal by TCPP detection. Among the ten samples characterized as normal or metaplastic based on the PAP-staining procedure, four samples demonstrated that same morphology using the TCPP method. Samples diagnosed as normal showed minimal or no TCPP uptake.

TCPP uptake in cells determined to be negative or metaplastic by cytomorphology had characteristic fluorescence intensity and patterns that were recognizable and diagnostic. Table 2 presents a comparison between cell morphology and fluorescence as determined by PAP-staining cytomorphology and TCPP techniques, respectively. Based on fluorescence intensity and pattern in TCPP-treated cell samples, cells were categorized with one of 14 possible numbered-classifications relating to a morphological description. If cells were class 11 using the TCPP determination and fewer than 2-3% of the cells on the slide were fluorescent above background levels, then that sample was determined to be metaplastic and not dysplastic. The metaplastic cells were easily differentiated from normal cells by their moderate fluorescence with a barely visible cell membrane. Of the ten cell samples that were determined to be negative or metaplastic by PAP-staining, 6 were designated with a class 11 cell description based on TCPP fluorescence. Of the six TCPP samples with class 11 designation, three also indicated fluorescence from nuclear debris (i.e., either a class 13 or 14), and two also showed class 10 designation (fluorescence from the nucleus only).

Another pattern shown in Table 2 relates to numerical classification 6—Irregular anisoid cells, low to medium fluorescence. It is notable that relatively few dysplastic cells were assigned this classification, while most carcinomic cells received classification 6. Hence, this classification is expected to be of particular importance in distinguishing carcinomas from dysplasias using the methods of the invention.

Another significant observation revealed in Table 2 is that, as cell morphology progressed from normal to severely carcinomic, the total number of numerical classifications that were assignable to each examined cell also increased. As an illustration, cells having a negative or metaplastic morphology were assigned an average of 2 numerical classifications, while cells displaying adenicarcinoma, squamous cell and small cell carcinoma were assigned an average of 5 numerical classifications. Since the numerical classifications contain descriptions of different kinds of cellular abnormalities, a positive correlation between degree of dysplasia or carcinoma and the number of different abnormalities observed in the cells is logical. However, such a correlation heretofore has not been systematized and used to diagnose precancerous and cancerous conditions in a sample of cells.

TABLE 1

Correlation Between TCPP Results and Cytomorphological Results.

| Diagnosis Description | N = 60<br>Slides with morphology using TCPP/<br>Slides with morphology using cytomorphology |
|---|---|
| Negative or metaplastic | 4/10 |
| Mild dysplasia | 12/12 |
| Moderate dysplasia | 9/9 |
| Severe dysplasia | 8/8 |
| Carcinoma in situ | 11/11 |
| Adenocarcinoma, squamous cell and small cell carcinoma | 10/10 |

TABLE 2

Cell descriptions: Cytomorphological Characteristics and TCPP Fluorescence.

| | Number of Samples with Cells having Numerical Description by TCPP Fluorescence Microscopy/ Number of Samples with Cell Description by Cytmorphology | | | | | |
|---|---|---|---|---|---|---|
| Classification Number = Cell description | Negative or metaplastic (n = 10) | Mild dysplasia (n = 12) | Moderate dysplasia (n = 9) | Severe dysplasia (n = 8) | Carcinoma in situ (n = 11) | Adenicarcinoma, squamous cell and small cell carcinoma (n = 10) |
| 1 = Large nucleus or nuclei, low to medium fluorescence | 3/10 | 12/12 | 9/9 | 7/8 | 10/11 | 6/10 |
| 2 = Symmetrical binuclear cells, medium fluorescence | 0/10 | 5/12 | 5/9 | 3/8 | 3/11 | 2/10 |
| 3 = Small oval cells, medium to high fluorescence | 0/10 | 4/12 | 4/9 | 2/8 | 6/11 | 6/10 |
| 4 = Small round cells, low fluorescence | 0/10 | 0/12 | 0/9 | 0/8 | 0/11 | 2/10 |
| 5 = Multi-nucleated cells, medium fluorescence | 0/10 | 0/12 | 3/9 | 6/8 | 9/11 | 7/10 |
| 6 = Irregular anisoid cells, low to medium fluorescence | 0/10 | 0/12 | 1/9 | 1/8 | 10/11 | 7/10 |
| 7 = Cellular clusters, medium to high fluorescence | 0/10 | 0/12 | 1/9 | 0/8 | 1/11 | 3/10 |
| 8 = Degenerated single cells, medium to high fluorescence | 0/10 | 0/12 | 0/9 | 0/8 | 4/11 | 7/10 |
| 9 = Degenerated cell clusters, medium to high fluorescence | 0/10 | 0/12 | 0/9 | 0/8 | 1/11 | 4/10 |
| 10 = Cells uniform size with small round nucleus, medium fluorescence (nucleus only) | 2/10 | 2/12 | 2/9 | 1/8 | 1/11 | 2/10 |
| 11 = Cell membrane barely visible, medium fluorescence | 6/10 | 6/12 | 2/9 | 2/8 | 2/11 | 0/10 |
| 12 = Nuclear debris clumps, no fluorescence | 0/10 | 1/12 | 0/9 | 0/8 | 0/11 | 0/10 |
| 13 = Nuclear debris background, no fluorescence | 6/10 | 5/12 | 8/9 | 2/8 | 5/11 | 3/10 |
| 14 = Nuclear debris background, medium fluorescence | 1/10 | 2/12 | 2/9 | 1/8 | 1/11 | 0/10 |
| Avg. # numerical descriptions per cell examined | 1.80 | 3.08 | 4.11 | 3.13 | 4.82 | 4.90 |

Each cell sample may be designated with more than one of the 14 numerical cell descriptions for TCPP-treated cells.

Suspension Assay for Detection and Separation of Pre-Cancerous and Cancerous Cells Using TCPP This example discloses the use of TCPP staining in conjunction with fluorescence flow cytometry in combination with cytomorphologic slide microscopy to determine the abnormality of cells found in sputum samples. By virtue of the specificity of TCPP staining, the combination of flow cytometry followed by slide microscopy is particularly powerful, providing an internal control for cytomorphologic slide comparisons.

Methods

Sputum Processing Procedures Used in Production of Suspensions and Monolayer Slides.

All suspensions and monolayer slides are produced from sputum samples collected through patients performing the early morning, spontaneous cough technique. Specifically, patients are instructed to expectorate whatever material they cough up across three consecutive mornings into a container filled with fixative consisting of 2% Carbowax in 50% alcohol/50% Saccomanno fluid with 0.03-0.05 mg/mL rifampin. Rifampin is added to the fixative solution to serve as a prophylactic against patients harboring *M. tuberculosis* or those patients who may be asymptomatic carriers of *N. meningitis*.

The 2% Carbowax solution is prepared by adding 2 mL melted Carbowax (150) to 98 mL of 50% ethanol and mixing for 30 minutes. Glassware used to make solution is kept warm to prevent hardening of wax on the surface during preparation, which can cause inaccurate measurement. Carbowax is removed before exposure to the TCPP working solution by immersion in 95% alcohol for at least 15 minutes.

Rifampin solution (3 mg/mL) is made by dissolving 300 mg capsules of rifampin into 100 mL ethyl alcohol and blending at high speed in a Waring blender. One mL of this solution is added to each 30 mL of Saccomanno solution or 20 mL per liter of Saccomanno solution and mixed thoroughly. The preparation of Saccomanno solution is according to standard methods well known to those in the art of cytology.

The sputum specimen is poured into a 50 mL plastic centrifuge tube and additional 50% ethyl alcohol solution added to bring the volume to 50 mL if necessary. The contents of the centrifuge tube are poured into a 250 mL Eberbach semi-microblender container and homogenized for 10 to 60 seconds, depending upon visual examination of the specimen and mucoid content. Thick mucoid specimens sometimes required longer blending times. The specimen is poured back into the centrifuge tube and centrifuged at low speed for 10 minutes. The supernatant is decanted, leaving 1 to 2 mL in the centrifuge tube to admix with the cell pellet. The tube is agitated on a vortex mixer for approximately 10 seconds. The sample is resuspended in 100 mM MES buffer, pH ~6.15. The cells are spun and rinsed two more times with 100 mM MES buffer, the last time leaving ~1 mL in the centrifuge tube in which to resuspend the cells. The cells are then resuspended in 15 ml 95% ethanol (5% 100 mM MES buffer) at room temperature (~20° C.) for 30 minutes, with gentle agitation. The centrifuge tube is then centrifuged at low speed for 10 minutes. All but 1-2 ml of the supernatant is removed.

TCPP Stock Solution.

400 mg of sodium bicarbonate is added to approximately 90 mL of the 50% isopropanol (50 mM sodium bicarbonate) and mixed until completely dissolved to make basified 50% isopropanol. One hundred milligrams of TCPP are slowly add to the basified 50% isopropanol (50 mM sodium bicarbonate) and mixed for 3 to 5 minutes until dissolved. The TCPP solution is brought to 100 mL volumetrically with the basified 50% isopropanol, mixed well and stored in an amber reagent bottle covered in foil in a refrigerated area. The final concentration of TCPP in the stock solution is 1 mg/mL.

TCPP Working Solution.

Fresh TCCP working solution is prepared each day. Approximately 10 mL of TCPP Stock Solution with concentration 1 mg/mL is brought to room temperature. Eight milliliters of the TCPP Stock Solution (1 mg/mL) are placed in a 200 mL volumetric flask and approximately 100 mL of the MS buffer is slowly added. The solution is gently mixed.

Additional MES buffer is added to bring the solution to 200 mL volumetrically. The solution is mixed for 3 to 5 minutes and stored at 2-4° C. in an amber bottle. The final concentration of TCPP in the working solution is 40 µg/mL.

TCPP Exposure Procedure.

Suspension cells, previously exposed to 95% alcohol for 30 minutes at room temperature, are exposed to TCPP immediately after fixing or up to 3 days later. The cells are resuspended in 10 ml of 40 µg/mL TCPP solution for 10 minutes at 36° C. with gentle agitation, then washed with 20 ml of room temperature, 100 mM MES buffer three times, using centrifugation at minimum speed to loosely pellet the cells within 10 minutes. The washed cell pellet is resuspended in 15-10 ml of MES buffer. These suspensions, or aliquots thereof, are passed through a fluorescence flow cytometry apparatus.

Fluorescence Flow Cytometry.

First Pass. A minimum of 10,000 cells are passed through a flow cytometer with cell sorting capability. The flow cytometer should be equipped with a light source providing radiation at about 415 nm, with filters to allow passage of light between about 390 nm and 490 nm. Fluorescence emission should be monitored between about 630 nm and 730 nm (emission maxima at 645 nm and 706 nm). A barrier filter passing light above 500 nm is satisfactory. On the first pass, individual cells are counted and their specific fluorescence measured. The average fluorescence is calculated, and the standard deviation from that average is calculated. Also, the median value is determined (the specific fluorescence value that is smaller than half the values and greater than half the values).

Fluorescence Flow Cytometry with Cell Sorting.

Second Pass. A minimum of 100,000 cells are passed through the fluorescence flow cytometer with cell sorting capability, equipped the same as for the first pass. Cells with fluorescence less than the Median fluorescence +1.3 standard deviations from the mean (approximately 90% of the cells) are operationally defined as having low fluorescence, and are saved in one test tube, and cells with specific fluorescence greater than or equal to the median fluorescence +1.3 standard deviations from the mean (approximately 10% of the cells) are operationally defined as having high fluorescence and are saved in another test tube. Alternatively, cells can be sorted into tubes according to their fluorescence relative to the median specific fluorescence found in the first pass. Cells with less than twice the median specific fluorescence would be "normal" or low fluorescence, and then cells could be pooled with 2-4×, the median fluorescence, 4-6×, and greater than 6× median fluorescence. Each of the higher intensity fluorescence pools would be expected to be more greatly enriched in abnormal cells. If more than 2-3% of the cells possessed more than 3× the median fluorescence, there would be support for a presumption of at least an advanced precancerous condition.

Production of Monolayer Slides.

The low- and high-fluorescent cell samples are centrifuged for 10 minutes at low rpm to pellet the cells. The supernatant is removed, leaving 1-2 mL in the centrifuge tube to admix with the cell pellet. The tube is agitated on a vortex mixer for approximately 10 seconds. One to three drops of the sediment is placed into a PreservCyt vial (Cytyc Corporation, Marlborough, Mass.). The specimen is incubated for 5 minutes to deactivate all microbial and viral organisms.

Monocellular layers of the samples are fixed onto slides using the Thinprep Processor (CYtyc Corporation, Marlborough, Mass.) according to the manufacturer's instructions. In the ThinPrep Processor, cells are collected onto a polycarbonate filter (pore size 0.5 mm) and transferred to a glass slide. The ThinPrep Processor then immediately deposits the slides into a fixative bath containing 95% ethanol (maintain for 30 minutes).

Sputum Slide Staining Procedures by Modified PAP-Staining Technique.

Procedure sequence (no.), reagent and time (min.:sec.) are as follows: (1) 95% alcohol 15:00; (2) tap water 1:00; (3) gil-i hemotox 2:30; (4) tap water 1:00; (5) bluing reagent: 30; (6) tap water 1:00; (7) 95% alcohol: 10; (8) og-6 1:30; (9) 95% alcohol: 10; (10) 95% alcohol: 10; (11) ea-50 1:15; (12) 95% alcohol: 20; (13) 95% alcohol: 30; (14) 100% alcohol 1:00; (15) 100% alcohol 1:00; (16) 100% alcohol 1:30; (17) xylene 1:00; (18) xylene 1:00; and (19) xylene 1:00.

Methods for Routine Cytopathological Analysis of Papanicolaou-Stained Slides.

PAP-stained slides undergo semi-quantitative cytomorphological evaluation. (1) dysplastic and neoplastic cells are identified through use of traditional morphologic criteria, and (2) the expression levels of seven fundamental indicators of pulmonary inflammation (alveolar macrophages, neutrophils, columnar cells, mucus, mucous spirals, pigmented macrophages, metaplastic cells) are quantified. The methodology for quantifying these inflammation indicators have been previously discussed in the literature (Roby et al., 1989, *Acta Cytol* 34:147-154; Roby et al., 1990, *Acta Cytol* 34:140-146; Schumann et al., 1989, *Am Rev Respr Dis* 139:601-603). The criteria used to determine cell morphology using PAP-stained cytology are discussed below.

No Significant Abnormalities.

Cells are identified as having no significant abnormalities if the following criteria are satisfied:
1. basophilic, ciliated epithelial cells admixed with macrophages with grade 1-2 pigment along with inflammatory cells;
2. round nuclei of epithelium basally oriented;
3. evenly dispersed chromatin;
4. inconspicuous nuclear membranes;
5. inconspicuous nucleoli; and
6. no metaplastic and no dysplastic cells present.

Squamous Metaplasia (without Dysplasia).

Cells are identified as squamous metaplastic without dysplasia if the following criteria are satisfied:
1. clumps of basophilic cells without cilia;
2. uniform cell and nuclear size;
3. low nucleus/cytoplasm (N/C) ratio;
4. nuclear chromatin finely granular; and
5. small rounded nucleoli (usually single) may be present.

Mild Dysplasia (Squamous Atypia).

Cells are identified as mildly dysplastic if the following criteria are satisfied:
1. smaller than metaplastic cells;
2. seen in cohesive clusters, or singularly;
3. cells lie flat (sheets) both nuclei and cytoplasm in focus;
4. cells vary slightly in size;
5. cytoplasm may be eosinophilic or basophilic;
6. cytoplasmic borders sharp;
7. nuclei vary slightly in size, usually round to oval, if divided 2 halves of nucleus are mirror images, N/C ratio may vary slightly;
8. nuclear membrane smooth;
9. nuclear chromatin (slightly increased) finely granular, occasional chromocenter; and
10. fiber cells, elongated cells with stretched cytoplasm and nucleus distinct nuclear membrane—fine reticular to granular cytoplasm usually bright yellow orange—keratinizing single, may form whorls around central core of keratin to make epithelial pearls.

Moderate Dysplasia (Squamous Atypia).

Cells are identified as moderately dysplastic if the following criteria are satisfied:
1. variation in size, usually larger but may be smaller than mild dysplasia;
2. more variation in shape and N/C ratio than mild dysplasia;
3. cytoplasm dense, acidophilia predominates; increased number of atypical cells;
4. nucleus may have unequal halves (not mirror images);
5. nuclear lobulations, crevices, and nodules are present; and
6. nuclear material may show hyperchromasia with more stippled—like chromatin pattern.

Severe Dysplasia (Marked Squamous Atypia).

Cells are identified as severely dysplastic if the following criteria are satisfied:
1. cells vary markedly in size and shape;
2. usually slightly larger cell size than moderate dysplasia;
3. N/C ratio is high but variable (with extremes);
4. single cells predominate; nucleus is more central than CIS;
5. nucleus may follow shape of cytoplasm; nucleus shows less distortion than CIS;
6. nuclear pleomorphism is increased with coarse chromatin present and condensation along nuclear envelope;
7. parachromatin, large nucleus, multi-nuclustered nuclear membrane focally thickened; and
8. cells show predominant acidophilic cytoplasm.

Carcinoma In-Situ Squamous (CIS, Non-Invasive).

Cells are identified as being carcinoma in situ squamous if the following criteria are satisfied:
1. cells single or in aggregates (clumps);
2. cell size variable may be smaller or larger than marked dysplasia cells usually smaller than invasive squamous cell carcinoma;
3. cells are large, rounded with symmetrically located nucleus;
4. cell degeneration may be present;
5. scant cytoplasm, distributed uniformly may be keratinized or non-keratinized concentrically around the nucleus, (orangiophilic or basophilic);
6. N/C ratio variable—higher or lower than normal;
7. coarse dense nuclear chromatin granules may be interrupted by clear zones;
8. uniformly thickened chromatinic rim with undulation of nuclear membrane;
9. lobulations of nuclei may be seen;
10. cannibalism may be seen, but is unusual;
11. multinucleated cells may be present;
12. no nucleoli in nucleus; a mitotic cell may be present; and
13. clean background.

Squamous Cell Carcinoma (Well Differentiated Keratinizing Type-Invasive).

Cells are identified as squamous cell carcinoma if the following criteria are satisfied:
1. cells usually single, orangeophilic, but may be in clusters, and degenerate;
2. cells large or small, angular, with well preserved nuclei and distinct cell borders;
3. cells usually larger than in-situ, and may be pleomorphic, wide range of both size and shape;
4. pearl formation may be seen (cancer pearl);
5. moderate amount of cytoplasm with abnormal "tailing" (consistent with invasion); bizarre cell shapes—tadpole, star, spindle; a nuclear chromatin angular, with unpredictable clumping with hyperchromasia and parachromatin clearing and clearly defined chromatin, parachromatin interface;
6. chromatin is coarsely clumped, especially along the nuclear membrane;
7. nucleoli are large and acidophilic, if present;
8. nuclear membrane itself may be thickened and irregular; irregularity of thickness of nuclear chromatin rim;
9. N/C ratio is very high;
10. marked nucleolar irregularity in shape, size, numbers (daughter nucleoli); abnormal mitoses, multi nucleation;
11. cannibalism and multinucleation is common; and
12. necrotic background material is common.

Cytopathology Analysis.

Because sputum samples contain cells from many locations in the lung, interspersed with each other, there is little context for judging the normality or abnormality of a particular cell (unlike the case for thin section staining). The availability of a collection of low-fluorescence cells provides an internal control sample of normal or nearly normal patient cells, with which to compare the high-fluorescence TCPP-stained cells. Using the standard PAP-stain, a cytopathologist skilled in the art can readily determine the degree of abnormality of the high-fluorescence TCPP cells, which are 10-fold enriched for abnormal cells compared with an un-fractionated monolayer.

The present invention is not limited to the embodiments described and exemplified above, but is capable of variation and modification within the scope of the appended claims.

What is claimed is:

1. A method to determine if a sample of cells contains dysplastic or carcinomic cells, the method comprising the steps of:
   contacting the sample with a solution of 5,10,15,20-tetrakis(carboxyphenyl) porphine (TCPP) under conditions permitting binding of the TCPP to components of the dysplastic or carcinomic cells, if any are present, wherein the solution of TCPP comprises the TCPP pre-dissolved in basified alcohol; and
   detecting TCPP fluorescence in the sample, the presence of TCPP fluorescence being indicative that the sample contains dysplastic or carcinomic cells.

* * * * *

UNITED STATES PATENT AND TRADEMARK OFFICE
CERTIFICATE OF CORRECTION

| | | |
|---|---|---|
| PATENT NO. | : 8,975,038 B2 | Page 1 of 1 |
| APPLICATION NO. | : 13/943476 | |
| DATED | : March 10, 2015 | |
| INVENTOR(S) | : Jeffrey Garwin | |

It is certified that error appears in the above-identified patent and that said Letters Patent is hereby corrected as shown below:

Title page, item 71 should read

--Applicant: bioAffinity Technologies, Inc., San Antonio, TX (US)--

Signed and Sealed this
Ninth Day of June, 2015

Michelle K. Lee
*Director of the United States Patent and Trademark Office*